United States Patent [19]

Murphy

[11] Patent Number: 4,656,333
[45] Date of Patent: Apr. 7, 1987

[54] THIN PROFILE SNOW, SLEET AND MOISTURE SENSING DETECTOR

[76] Inventor: John P. Murphy, 37508 Grove Ave., Willoughby, Ohio 44092

[21] Appl. No.: 687,123

[22] Filed: Dec. 28, 1984

[51] Int. Cl.$^4$ ............................................. H05B 1/02
[52] U.S. Cl. .................................. 219/209; 219/201; 307/118; 340/602
[58] Field of Search ....................... 219/200, 209, 201; 307/118; 340/602

[56] References Cited

U.S. PATENT DOCUMENTS

| | | | |
|---|---|---|---|
| 390,619 | 10/1888 | Ries ...................................... | 219/209 |
| 3,412,326 | 11/1968 | Jones et al. ...................... | 219/201 X |
| 3,440,396 | 4/1969 | Greene, Jr. .......................... | 219/201 |
| 3,500,059 | 3/1970 | Fielding et al. ..................... | 307/118 |

Primary Examiner—Howard N. Goldberg
Assistant Examiner—Taylor J. Ross
Attorney, Agent, or Firm—Baldwin, Egan & Fetzer

[57] ABSTRACT

A moisture sensing detector of snow, sleet, ice and rain. The detector includes a sensing probe and coacting control circuitry for receiving the moisture signal from the probe and actuating associated equipment such as, for example, a railroad switch heater. The probe includes sturdy substantially elongated electrically charged aluminum electrodes spaced apart a very small distance ($\frac{1}{8}''$ gap for example) by fiberglass strip insulation. Any moisture (even a drop of water) bridging the small gap completes a circuit between the electrodes which triggers the control circuit into actuating the railroad track switch heater or any like equipment. The electrodes are substantially elongated to provide a large sensing area. A heating unit is secured to one electrode to heat the entire length of the probe thereby melting any ice, sleet and snow (since they do not conduct an electrical current) thus permitting the probe to detect resultant moisture. The probe has a sharp upper edge cross sectional profile to forestall the accumulation of debris thereon. If debris should stay on the probe, its long length allows accumulation of significant amounts of debris without affecting sensitivity to moisture detection. A thermostat in the control circuitry turns on the probe at predetermined ambient temperature above the moisture freezing point.

In another embodiment, the heating unit structure is substituted for one of the electrodes in the probe.

17 Claims, 10 Drawing Figures

THIN PROFILE SNOW, SLEET AND MOISTURE SENSING DETECTOR

This invention relates to snow, ice and sleet detecting devices and more particularly to such a device for detecting the initial presence of snow, ice or sleet on the ground, on an exterior exposed structure, or the like, for the purpose of activating a heater or similar device to remove the snow, ice or sleet from the structure. The invention is described herein with reference to detecting snow, ice or sleet in the area of a railroad switch to activate a switch heater, although it is to be understood that the invention may be used in coaction with any application wherein the immediate detection of snow, ice, sleet or moisture is essential.

BACKGROUND OF THE INVENTION

This invention pertains to a moisture detecting probe particularly adapted for use as a part of a snow melter control system and, for purposes of exemplification, will be described in this connection. There has long been a need for means for detecting the presence of moisture, in the form of rain, sleet or snow, on surfaces which present a hazard under freezing conditions. For example, the occurrence of sleet or snow on bridges, parking lots, airport runways, sidewalks, railroad track switches, and so forth always presents a dangerous condition. To alleviate this condition, common practice has been to install heating cables. When frozen moisture conditions exist, the heating cables can be switched on, raising the temperature to melt the accumulated moisture and prevent unsafe conditions from arising.

A problem has existed in providing the necessary controls for automatically switching on and off the heating cables. Two conditions must exist before heating cables need to be switched on. That is, there must be the presence of water in some form, whether sleet, rain or snow, combined with freezing temperatures. The temperature may be detected in the surface itself or in the air above the surface. While the detection of temperature is relatively simple, a difficult problem has existed in detecting the presence of water. Prior probes become inoperative when debris accumulates thereon. Under severe snowing and snow drifting conditions, they also become inoperative because the ice, snow or sleet accumulates thereon and builds up like an igloo to the extent that prior probes are unable to melt the accumulating precipitation and are unable to detect new precipitation. In effect, in severe weather, these prior probes are effectively removed from being exposed to continuing or new precipitation by a build-up of snow or ice and are thus rendered ineffective for detecting such precipitation. Also, prior probes can not withstand heavy industrial uses.

It is the principal object of this invention to provide an improved moisture probe adaptable, as an example of its application, for use in a system to switch on and off heating cables or other similar devices.

A further object of the invention is to provide a moisture sensing probe constructed to forestall accumulation of debris thereon, yet if any debris should accumulate on the probe, its structure permits continued operation.

A further object of the invention is to provide a moisture sensing probe having heating means to heat the entire length of the electrodes under freezing conditions to assure continuous operation of the probe.

A further object of the invention is to provide a heating probe of very sturdy construction to withstand heavy industrial use.

A further object of the invention is to provide a moisture sensing probe of the above type that is simple in construction, inexpensive to manufacture, and highly effective in operation.

BRIEF DESCRIPTION OF THE INVENTION

Briefly, the foregoing objects are accomplished by the provision of a snow detector and control system to detect the presense of snow, ice, freezing rain, sleet, or blowing snow, etc. on the ground or on an exterior exposed structure, under freezing conditions, which detection is used to operate circuitry to, in turn, switch or operate other equipment such as, for example, a railroad track switch heater.

Liquid water is a conductor, a very feeble conductor, and the presence of liquid water can be detected by measuring the passage of a current through liquid water. Frozen water, e.g. ice, snow, etc. does not conduct an electrical current. The snow detector and control system of the invention senses the presence of liquid water under freezing conditions and, through circuitry activated by this sensing of water, operates electrically other switches to operate associated equipment. For instance, at freezing conditions, solid water such as ice or snow are melted with the invention by the application of heat to convert the solid water to liquid water whose presence can be determined as noted earlier.

The current invention employs the use of very sensitive electronic circuitry to detect the presence of liquid water by sensing a very small current passing through the water and then activating other circuitry as described earlier when this small current is detected.

This disclosure includes two major components which are (1) the electronic/electro mechanical sensing and control circuitry and (2) the sensing probe.

The electronic/electro mechanical sensing and control circuit contains an electronic solid state switch that is operated by establishing a conductive path between the probe terminal and ground (2 megohms or less). This utilizes a small current (less than 20 microamperes at 0.5 megohms) which electronically gates an AC semiconductor device which is the sensing unit switching element. Internal RC snubber, choke and thyrector components provide effective protection from typical transients. Associated with this solid state electronic component are related electro mechanical devices such as relays, and/or a time switch, and terminal blocks. This control unit assembly is connected electrically to the sensing probe.

The sensing probe consists of two large elongated electrodes separated or spaced electrically from each other, the separation of which may be bridged by water (even one drop of water) or other similar conductors. The separation can be by an air gap or some solid electrically non-conducting separator such as a ceramic, plastic, or non-metallic solid separator. The two electrodes constitute the open part of the conductive path. The sensing probe is heated so that it remains above 32° F. (0° C.), and is preferably heated above 100° F. and up to 160° F. or higher.

The sensing probe of the invention consists of a heavy aluminum right-angle support, to which is attached an energized electrical heating element, an electrode (narrow aluminum bar near the top of the extrusion pictured) and electrical connections to the electronic sensing component noted above. The two electrodes (aluminum right-angle extrusion and narrow bar) are separated from each other by a non-conducting fiberglass insulator for the entire length of the aluminum bar. The fiberglass insulator is flush with the top of the aluminum bar and extends continuously between the bar and the right-angle extrusion.

The probe is heated to about 150° F. with a metal sheathed heating element bolted to the right-angle extrusion. The two electrodes (right-angle extrusion and aluminum bar) are in the conductive path between the probe terminal and ground as noted for the electronic component above described.

When liquid water bridges the space between the two electrodes, the conductive path is completed. The conductivity of water, even as little water as one drop or even the presence of dampness, is sufficient to operate the electronic switch. Operating the electronic switch in turn operates a relay to start or stop whatever equipment is to be operated by the snow detector.

Many aspects of the sensing probe are particularly advantageous. A large sensing area, in this instance as a long length, allows the accumulation of significant amounts of debris or insulating material which might interfere with the conductive path of a probe having a significantly smaller area or length. Such large sensing area retains effective operation under dirty or undesirable conditions. Instead of being of long length, a similar length of probe sensing length could be abhieved by using round, concentric electrodes or electrodes with some other non-linear configuration. Likewise, the two segments of the conductive path could be made up of two stacked electronic circuit pairs. That is, the large sensing length/area is not to be restricted to the configuration just described. In practical applications such as railroad yards, falling grease, coal, etc. can be troublesome to prior sensing devices which rely on very small air-gap bi-electrode sensing probes. These are subject to much maintenance and cleaning for effective operation. In many instances, the referred to small probed sensors do not function effectively because they are blinded by debris. With the present invention the two electrodes present an upper very narrow elongated structure which causes debris to fall to the sides of the probe.

Until this invention, prior snow detectors operated with low heating, e.g. 40° F. This low level of heat allows the accumulating of grease, oil, and even allows building up of snow over the entire sensing unit when heavy snows occur. The effect of covering such smaller sensors operating at low temperature is to render them inoperative since, under the conditions described, they are unable to detect the presence of new precipitation. In contrast, the higher temperature probe of this invention melts or oxidizes and evaporates falling grease and oil, maintaining the probe in an operative condition. The higher probe temperature of this invention provides sufficient heat so that even very heavy falling snow cannot blind or "igloo" the probe to prevent it from seeing and sensing actual weather conditions.

Other objects and advantages of the invention will be apparent from the following description taken in conjunction with the drawings wherein:

BRIEF DESCRIPTION OF THE DRAWINGS

FIG. 6 is a perspective view showing the moisture sensing probe of the invention and its sensing and control circuitry box connected to railroad track switch heater; and FIG. 7 is a simplified schematic wiring diagram illustrating an application of the moisture probe of the invention.

In the drawings, like numbers and letters are used to identify like and similar parts throughout the several views.

DESCRIPTION OF THE PREFERRED EMBODIMENTS

Figure 1:
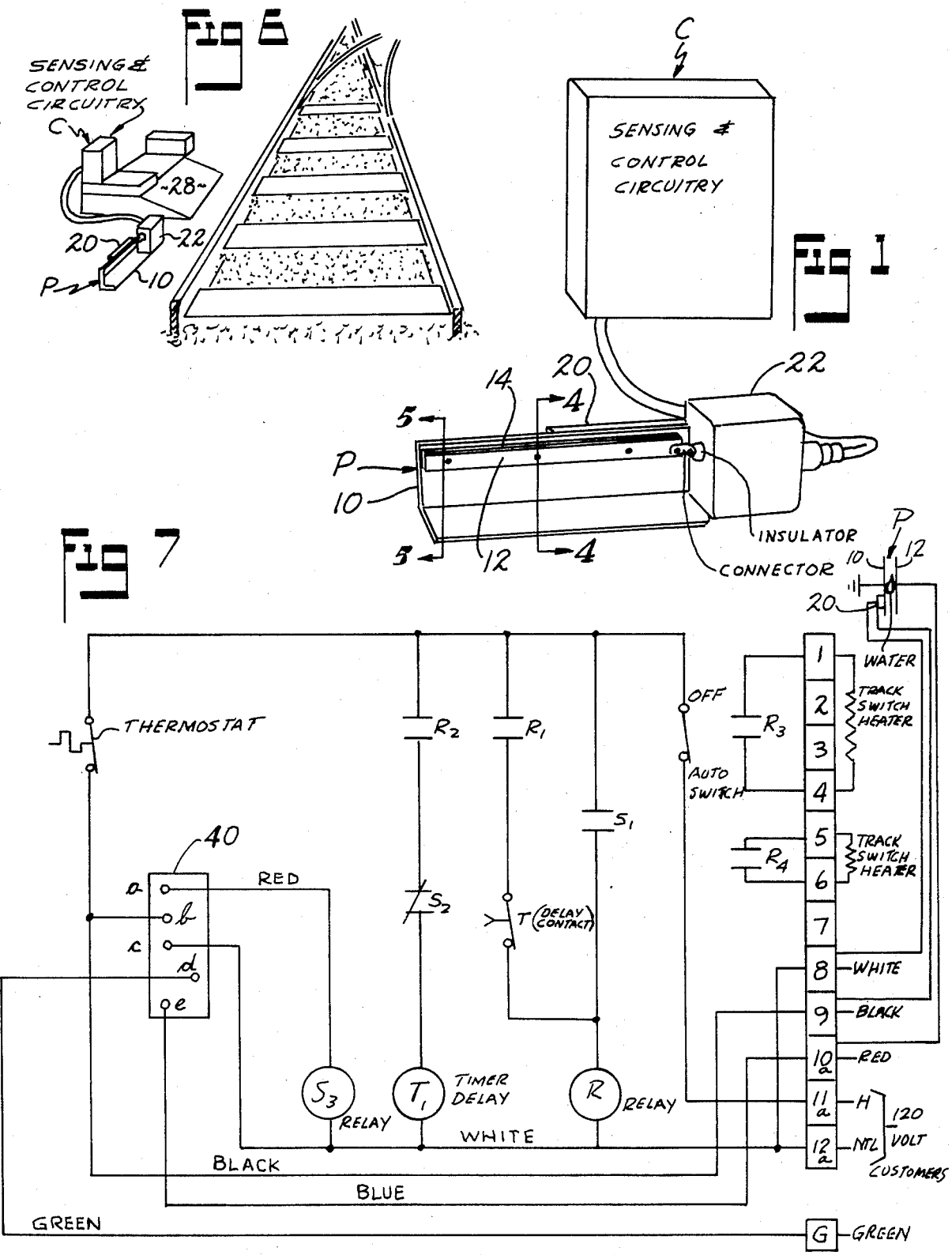
FIG. 1 is a perspective view of a moisture sensing probe constructed in accordance with the invention and showing the probe electrically connected to a sensing and control circuitry box.
Figure 2:
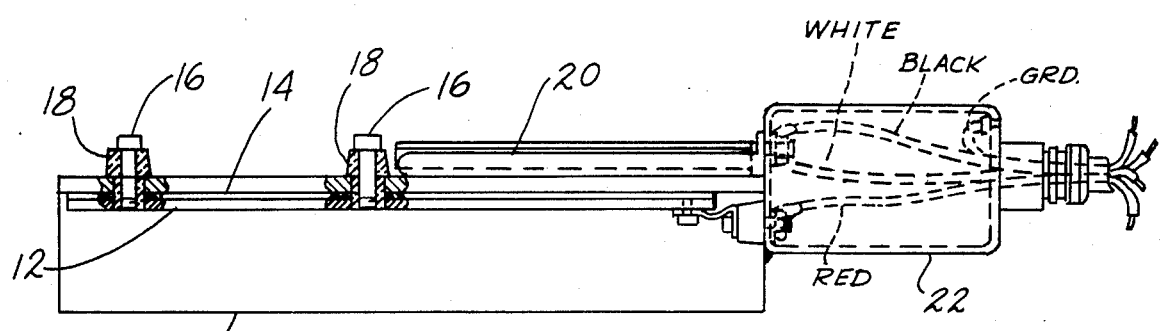
FIG. 2 is a top plan view, partly in section, of the probe shown in FIG. 1.

Referring first to FIG. 1, there is shown a moisture sensing probe of the invention, generally designated as P. The probe P is electrically connected in FIG. 7. The sensing and control circuitry C is not to a sensing and control circuitry box generally designated as C, the wiring diagram thereof being shown described herein in detail as the same, per se, does not form the invention.

The probe P includes a pair of elongated planar electrodes 10 and 12 (FIGS. 1–4) which are retained in spaced relation by a fiberglass insulator 14 interposed therebetween, such assembly being secured together by the screws 16 which are contained within the ceramic insulators 18.

The electrode 10 is in the preferred form of a heavy aluminum extruded right-angle support which also functions as the base of the probe. This construction provides substantial sturdiness to the probe for heavy industrial use. The electrode 12 is an aluminum strip. Although aluminum is the preferred material for the electrodes, any other suitable material may be used that will provide a sturdy structure.

Secured to the back side of the electrode or right-angle support 10 is a heating element 20 which functions to heat the entire length of both electrodes 10 and 12 to a preferred temperature range of 120° F. to 180° F. to melt ice, sleet and snow falling on the electrodes. It obvious that the heating element could comprise one of the electrodes.

As shown in FIG. 1, a junction box 22 is secured to the right-angle support electrode 10 to house the electrical connections from the sensing and control circuitry box C.

Figure 5:
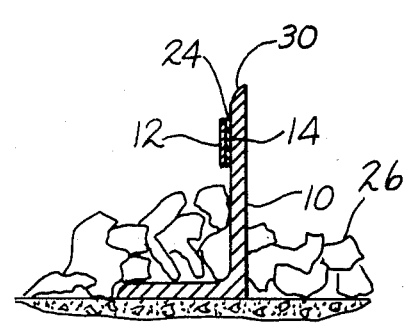
FIG. 5 is a view taken along the line 5—5 of FIG. 1.
Figure 4:
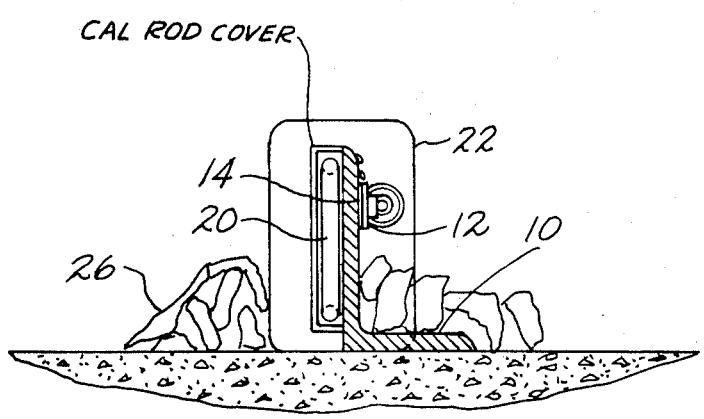
FIG. 4 is a view taken along the line 4—4 of FIG. 1.

Accordingly, the invention provides a moisture sensing probe P including a pair of planar substantially elongated electrodes 10 and 12 disposed in spaced parallel relation and spaced apart a very small predetermined distance (gap 24) to detect a drop of water or minute amount of moisture bridging such gap therebetween. The preferred spacing of the gap 24 is approximately ⅛ of an inch or less. The planar electrodes 10 and 12 are positioned in side-by-side vertical parallel relation whereby each electrode has a moisture sensing thin edge exposed upwardly providing a minimum and very narrow exposed top surface of the probe, as best shown in FIG. 5, to prevent debris 26 from accumulating on top of the probe. This provision of narrow top exposed surfaces of the probe electrodes without substantial upwardly facing support areas adjacent the electrodes, aids in preventing debris, which may include oil and grease, from accumulating on top of the probe and blinding the probe, as aforementioned, and as generally shown in FIGS. 4 and 5 of the drawings. The heating element 20 is secured to at least one of the electrodes to maintain the temperature of the entire length of the electrodes 10 and 12 at a preselected temperature above the moisture freezing point.

Sensing and control circuitry C is electrically connected to the electrodes 10 and 12 for sensing moisture between and bridging the electrodes and actuates associated equipment in response to such moisture sensing. In FIG. 6, for example, the probe P and its sensing and control circuitry C are connected to the heater of a railroad track switch operating mechanism 28, although it is to be understood that the invention may be applied to any application wherein the detection of ice, sleet and snow is desired.

Figure 3:
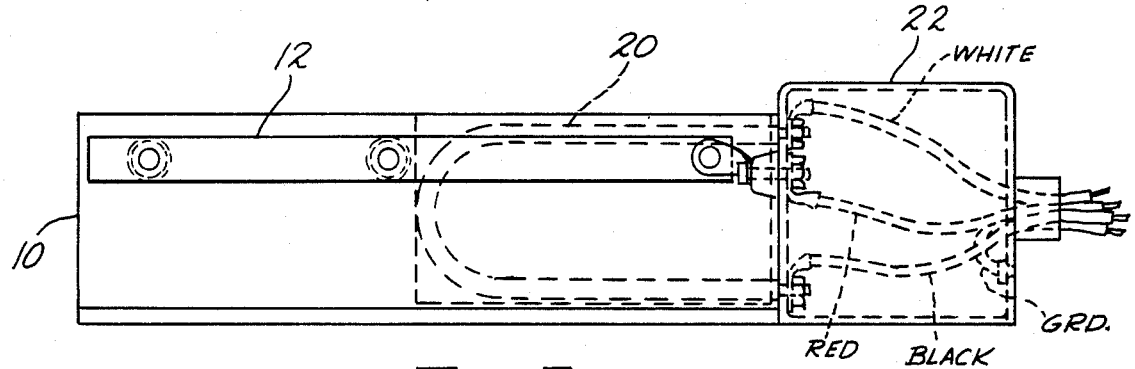
FIG. 3 is a side elevational view of the probe shown in FIG. 1.

In the preferred form, the electrode 12 is secured to the electrode 10 below the top edge of electrode 10, as best shown in FIGS. 3 and 5, to present a very narrow ledge to further reduce the chances of debris accumulation. Additionally, the electrode 10 has its top edge 30 tapered forming an upwardly exposed knife edge to cause debris 26 to fall downwardly to the sides of the probe.

The sensing and control circuitry C includes a thermostat (FIG. 7) and associated circuitry to turn on the heating element 20 at a predetermined ambient temperature a few degrees Fahrenheit above the freezing point of the moisture and to activate the probe P.

In a modification of the invention, the electrodes may be a foil of aluminum or other metal deposited on an insulator.

It is to be understood that the probe electrodes should be formed of materials (such as metal) that are generally heat conductive as well as being sturdy. Such heat conductiveness is necessary for the heating element 20 to heat up the entire length of the probe P.

In FIG. 7 the thermostat is set to turn on the probe heating element 20 (through connector block terminals 8 and 9) when the temperature is about 34° F. to 40° F., for example, to melt ice or snow falling on the probe 20 and thus a water detection signal from the probe P is sent through connector block terminal 10a thence through the blue wire to terminal e of detector or sensor switch 40 which is a typical voltage comparator-triac type ground sensing switch that is readily available on the market. The switch 40 is thus turned on and power is now applied through its terminals a and b thereof. Power through the red wire energizes the coil of relay S3. S3 closes relay S1 to energize the coil of relay R. When R coil is energized, it closes relay contact R1 locking in relay coil R. The delay contact T remains closed. When S3 coil is energized, it also opens normally closed contact S2 keeping the timer (coil) T1 deenergized. When relay R is energized, it also closes R2 (along with R1). When relay R is energized, track switch heaters R3 and R4 are turned on.

Figure 8:
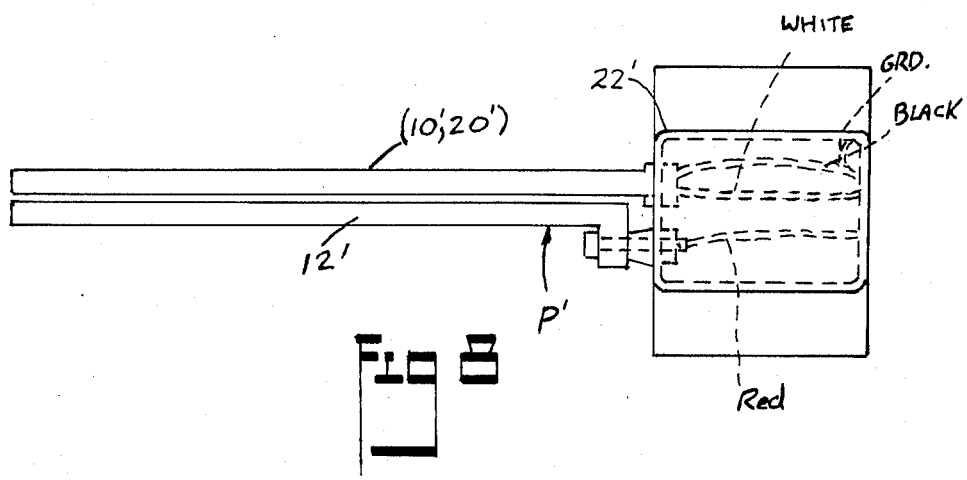
FIG. 8 is a top plan view of another embodiment of probe wherein the heater for the probe forms (i.e. is substituted for) one of the electrodes of the first described probe, with the combined heater-electrode being spaced from the other electrode of the probe.
Figure 9:
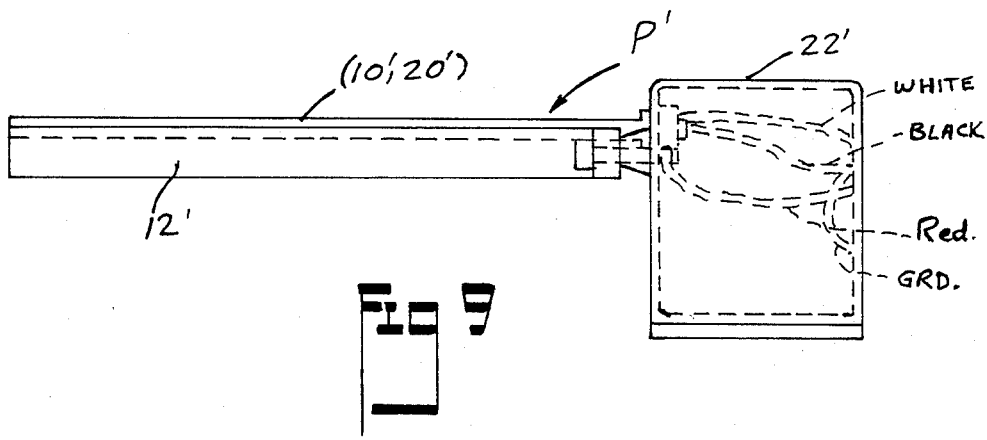
FIG. 9 is a side elevational view of the FIG. 8 embodiment.
Figure 10:
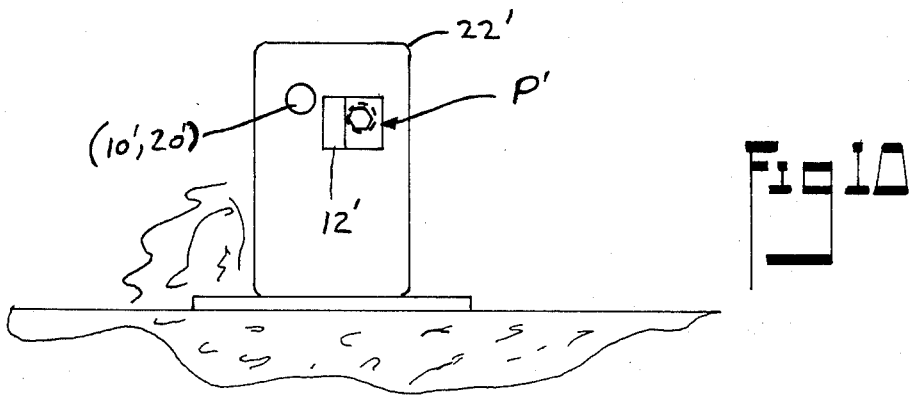
FIG. 10 is a front elevational view of the probe of FIGS. 8 and 9.

When the probe P no longer senses moisture, the signal from probe P is terminated returning the detector switch 40 to OFF position. This deenergizes coil S3 to return S2 contact to closed position which energizes timer T1. This condition continues until the coil of timer T1 times out and is deenergized. When this happens, the delay contact T opens to deenergize coil R which turns off track switch heaters R3 and R4. Again, the FIG. 7 circuit will not be further described in detail, as such circuit, per se, does not form the invention. The probe heater 20 could be easily wired in as one of the electrodes of probe P simply by connecting it to connector block terminal 10a and electrically insulating it from the other electrode, and as shown in FIGS. 8, 9 and 10. In these drawing figures, like reference numbers have been utilized for like parts referred to in the first described embodiment of probe, with the addition thereto of the prefix prime to the reference number. Thus in this alternate embodiment of probe, the heating element serves as (or forms) one of the electrodes resulting in a combined electrode-heater (10', 20') with the heating element winding being encased in the tubular outer structure of the combined electrode-heater. This heating element is analogous to the calrod heating element of FIGS. 1 to 4 of the first described embodiment of probe. The other electrode 12' of this modified probe P' may be a rectangular shaped rod similar to the corresponding electrode of the first described probe embodiment, disposed in closely spaced relationship to the combined electrode-heater element (10', 20') with the electrode 12' being insulated from the junction box 22' by an insulator, and generally similarly to that of the first described probe embodiment, with the electorde 12' being, in the embodiment illustrated, disposed below the upper edge or surface of the combined electrode-heating element (10', 20') for aiding in attempting to prevent debris accummulation on the probe, and likewise generally similar to that of the first described probe embodiment.

The junction box 22' of this modified probe in the embodiment illustrated, is supported on a flange which in turn is adapted to rest on a supporting surface, and in conjunction with the box, positions the electrodes of the probe above the supporting surface, and without substantial upwardly facing support areas immediately adjacent the moisture sensing surfaces of the electrodes, thus helping to facilitate the prevention of debris from accumulating on top of the electrodes of the probe and blinding the probe.

The terms and expressions which have been employed are used as terms of description, and not of limitation, and there is no intention, in the use of such terms and expressions, of excluding any equivalents of the features shown and described or portions thereof, but it is recognized that various modifications are possible within the scope of the invention claimed.

What is claimed is:

1. A moisture sensing probe comprising; a pair of elongated electrodes disposed in spaced generally parallel relation and spaced apart horizontally a very small predetermined distance to detect a drop of water or minute amount of moisture bridging the gap therebetween, said electrodes being positioned in side-by-side generally parallel relation whereby each electrode has a moisture sensing edge exposed upwardly, said probe including means for supporting said probe on a support and positioning said edges above the level of such support, said edges in conjunction with said means providing a minimum and very narrow top exposed surface of the probe without substantial adjacent upwardly facing supporting areas, to attempt to prevent debris from accumulating on top of the probe and between said electrodes, and blinding the probe.

2. A moisture sensing probe comprising; a pair of planar elongated electrodes disposed in spaced parallel relation and spaced apart a very small predetermined distance to detect a drop of water or minute amount of moisture bridging the gap therebetween, said planar electrodes being positioned in side-by-side vertical parallel relation whereby each electrode has a moisture sensing thin edge exposed upwardly providing a minimum and very narrow exposed top surface of the probe to prevent debris from accumulating on top of the probe, a heating element secured to at least one of the electrodes to maintain the temperature of the entire length of the electrodes at a preselected minimum or higher temperature above the moisture freezing point, sensing and control circuitry electrically connected to the electrodes for sensing moisture between and bridging the electrodes and actuating associated equipment in response to such moisture sensing, said gap being approximately ⅛ inch in width, and a fiberglass insulation strip disposed in the gap between the electrodes, one of said electrodes being formed of relatively thick aluminum to withstand heavy industrial use, and the other electrode being an aluminum strip insulatingly secured to said one electrode, said one electrode being an elongated right-angle structure, said other electrode being secured to said one electrode below the top edge of said one electrode, said one electrode having its top edge tapered forming an upwardly exposed knife edge to cause debris to fall downwardly to the sides of the probe, the heating element maintaining the temperature of the entire length of the electrodes at a temperature of approximately 120° F. to 180° F., said sensing and control circuitry including a thermostat and associated circuitry to turn on the heating element at a predetermined ambient temperature a few degrees Fahrenheit above the freezing point of the moisture.

3. A moisture sensing probe comprising; a pair of elongated electrodes disposed in spaced generally parallel relation and spaced apart a relatively small predetermined distance to detect a drop of water or minute amount of moisture bridging the gap therebetween, each of said electrodes having a generally upwardly facing moisture sensing surface, said probe including means for supporting said electrodes on a support and positioning said sensing surfaces above such support, said sensing surfaces being horizontally and vertically spaced relative to one another with the top surface of said probe being substantially devoid of upwardly facing supporting areas adjacent said electrodes, to aid in preventing debris from accumulating on top of the probe and between said electrode sensing surfaces, and blinding said probe, and a heating element for maintaining at least a portion of each of said sensing surfaces at a minimum or higher preselected temperature above the moisture freezing point.

4. A moisture sensing probe comprising; a pair of elongated electrodes disposed in parallel relation and spaced apart horizontally a very small predetermined distance to detect a minute amount of moisture bridging the gap bherebetween, said probe including means for supporting said electrodes on a support above the level of the latter, each said electrode having a moisture sensing edge exposed upwardly, said edges in conjunction with said means providing a minimum and narrow top exposed surface of the probe without substantial adjacent upwardly facing support areas, for attempting to prevent debris from accumulating on top of the probe and between said electrodes, and blinding the probe, and a heating element coacting with said electrodes to maintain the temperature of the electrodes at a preselected temperature above the moisture freezing point.

5. The structure of claim 4 wherein the heating element is operable to maintain the temperature of the entire length of the electrodes at a temperature of approximately 120° F. to 180° F.

6. A moisture sensing apparatus for sensing moisture under varying ambient temperature conditions comprising; a pair of horizontally spaced apart elongated electrodes each having at least one exposed moisture sensing surface; said electrodes being positioned in generally side-by-side generally parallel relation whereby each of said moisture sensing surfaces is exposed upwardly, said probe including means for supporting said probe on a support and positioning said sensing surfaces above the level of such support, said sensing surfaces in conjunction with said means providing a minimum and very narrow top exposed area of the probe without substantial adjacent supporting areas, thus helping to prevent debris from accumulating on top of the probe and blinding the same, a heating element secured to at least one of said electrodes for maintaining the temperature of the entire length of each electrode at a preselected temperature above 32° F.; and sensing and control circuitry electrically connected to said electrodes for sensing moisture between and bridging said electrodes and actuating associated equipment in response to such moisture sensing.

7. The structure of claim 6, wherein said sensing and control circuitry includes a thermostat and associated circuitry to turn on the heating element at a predetermined ambient temperature a few degrees Fahrenheit above the freezing point of the moisture.

8. A moisture sensing probe comprising; a pair of elongated generally planar electrodes disposed in spaced generally parallel relation and spaced apart a very small predetermined distance to detect a drop of water or minute amount of moisture bridging the gap therebetween, said planar electrodes being positioned in side-by-side vertically parallel relation whereby each electrode has a moisture sensing thin edge exposed upwardly, said probe including means for supporting said probe on a support and positioning said edges above the level of such support, said edges in conjunction with said means providing a minimum and very narrow exposed top surface of the probe without substantial adjacent upwardly facing supporting areas to attempt to prevent debris from accumulating on top of the probe and between said electrodes, and blinding said probe, and a heating element secured to at least one of the electrodes to maintain the temperature of the entire length of the electrodes at a minimum or higher preselected temperature above the moisture freezing point.

9. The structure of claim 8 wherein said gap is approximately ⅛ inch in width.

10. The structure of claim 8 and further including a fiberglass insulation strip disposed in the gap between the electrodes.

11. The structure of claim 8 and further including sensing and control circuitry having a voltage comparator-triac type ground sensing switch for receiving the moisture sensing signal from the probe and actuating associated equipment in response to such signal.

12. The structure of claim 8 wherein said heating element forms one of the electrodes.

13. A moisture sensing probe comprising; a pair of elongated generally planar electrodes disposed in horizontally spaced generally parallel relation and spaced apart a very small predetermined distance to detect a drop of water or minute amount of moisture bridging the gap therebetween, said planar electrodes being positioned in side-by side vertically parallel relation whereby each electrode has a moisture sensing thin edge exposed upwardly providing a minimum and very narrow exposed top surface of the probe prevent debris from accumulating on top of the probe, and a heating element secured to at least one of the electrodes to maintain the temperature of the entire length of the electrodes at a minimum or higher preselected temperature above the moisture freezing point, and wherein one of said electrodes is formed of relatively thick metal to withstand heavy industrial use, and the other electrode is a metallic strip secured to said one electrode.

14. The structure of claim 13 wherein the electrodes are formed of aluminum.

15. The structure of claim 13 wherein said one electrode is an elongated heavy aluminum right-angle support, L-shaped in transverse section.

16. The structure of claim 13 wherein said other electrode is secured to said one electrode below the top edge of said one electrode.

17. The structure of claim 16 wherein said one electrode has its top edge tapered forming an upwardly exposed knife edge to cause debris to fall downwardly to the sides of the probe.

* * * * *